US012734152B2

(12) United States Patent
Muthusamy et al.

(10) Patent No.: US 12,734,152 B2
(45) Date of Patent: Sep. 15, 2026

(54) SOLID STATE FORMS OF NIROGACESTAT SALTS

(71) Applicant: ASSIA CHEMICAL INDUSTRIES LTD., Tel Aviv (IL)

(72) Inventors: Anantha Rajmohan Muthusamy, Sivakasi (IN); Amit Singh, Greater Noida (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 308 days.

(21) Appl. No.: 18/712,286

(22) PCT Filed: Nov. 23, 2022

(86) PCT No.: PCT/US2022/050833

§ 371 (c)(1),
(2) Date: May 22, 2024

(87) PCT Pub. No.: WO2023/096954

PCT Pub. Date: Jun. 1, 2023

(65) Prior Publication Data

US 2024/0408067 A1 Dec. 12, 2024

(30) Foreign Application Priority Data

Nov. 23, 2021 (IN) ............................ 202111053832

(51) Int. Cl.

| | |
|---|---|
| ***C07D 233/64*** | (2006.01) |
| ***A61K 31/41*** | (2006.01) |
| ***A61K 31/417*** | (2006.01) |

(52) U.S. Cl.

CPC .......... *A61K 31/417* (2013.01); *C07D 233/64* (2013.01)

(58) Field of Classification Search

CPC ............................ C07D 233/64; A61K 31/417

See application file for complete search history.

(56) References Cited

FOREIGN PATENT DOCUMENTS

| | | | |
|---|---|---|---|
| WO | 2005092864 | A1 | 10/2005 |
| WO | 2021029854 | A1 | 2/2021 |
| WO | 2021146604 | A1 | 7/2021 |
| WO | 2021183934 | A1 | 9/2021 |

OTHER PUBLICATIONS

Jaakko Aaltonen, et al., "Solid form screening—A review", European Journal of Pharmaceutics and Biopharmaceutics, 2009, vol. 71(1), 23-37.

Lee, Eun Hee, "A practical guide to pharmaceutical polymorph screening & selection", Asian Journal of Pharmaceutical Sciences, 2014, 9(4), p. 163-175.

Mino R. Caira: "Crystalline Polymorphism of Organic Compounds", Topics in Current Chemistry, 1998, vol. 198, pp. 163-208.

Russian Office Action issued in corresponding application 2024116838 mailed May 29, 2026, together with English language translation.

Sarma B. et al., "Solid formation of pharmaceuticals: Polymorphs, salt and cocrystals", Korean J.Chem.Eng., 2011, 28 (2), p. 315-322.

Search Report issued in corresponding application 2024116838 mailed May 29, 2026, together with English language machine translation.

*Primary Examiner* — Shawquia Jackson

(74) *Attorney, Agent, or Firm* — Carter, DeLuca & Farrell, LLP

(57) ABSTRACT

The present disclosure encompasses solid state forms of Nirogacestat salts, in embodiments crystalline polymorphs of Nirogacestat salts, processes for preparation thereof, and pharmaceutical compositions thereof.

23 Claims, 9 Drawing Sheets

Figure 1: XRPD of Nirogacestat hydrobromide salt- Form NHBr1

Figure 2: XRPD of Nirogacestat hydrochloride salt- Form NHCl1

SOLID STATE FORMS OF NIROGACESTAT SALTS

CROSS REFERENCE TO RELATED APPLICATIONS

This application is a National Stage of, and claims priority to and the benefit of, International Patent Application No. PCT/US2022/050833, filed on Nov. 23, 2022, which, in turn, claims the benefit of and priority to, Indian Provisional Application No. 202111053832, filed on Nov. 23, 2021, the entire disclosures of each of which are incorporated by reference herein.

FIELD OF THE DISCLOSURE

The present disclosure encompasses solid state forms of Nirogacestat salts, in embodiments crystalline polymorphs of Nirogacestat salts, processes for preparation thereof, and pharmaceutical compositions thereof.

BACKGROUND OF THE DISCLOSURE

Nirogacestat, S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide, has the following chemical structure:

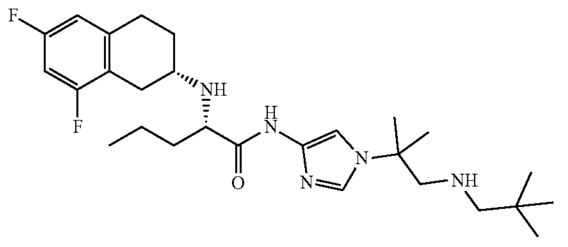 [SMILES: CCC[C@H](N[C@H]1CCc2cc(F)cc(F)c2C1)C(=O)Nc1cn(C(C)(C)CNCC(C)(C)C)cn1]

Nirogacestat (is a selective gamma secretase (GS) inhibitor with potential antitumuor activity. In particular, it has been investigated as a monotherapy for patients with desmoid tumors. Nirogacestat is also under investigation for the treatment of ovarian granulosa cell tumors, as well as relapsed or refractory multiple myeloma.

The compound is described in U.S. Pat. No. 7,795,447.

International Publication No. WO2021/029854 discloses polymorphs of Nirogacestat dihydrobromide salt and amorphous Nirogacestat dihydrobromide salt.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Nirogacestat and of Nirogacestat salts.

SUMMARY OF THE DISCLOSURE

The present disclosure provides crystalline polymorphs of Nirogacestat salts, processes for preparation thereof, and pharmaceutical compositions thereof. These crystalline polymorphs can be used to prepare other forms of Nirogacestat or of Nirogacestat salts.

The present disclosure provides crystalline polymorphs of Nirogacestat salts for use in the preparation of pharmaceutical compositions and/or formulations for use in medicine, in embodiment as an antitumor agent. In particular, as a monotherapy for patients with desmoid tumors, or as therapy for ovarian granulosa cell tumors, or relapsed or refractory multiple myeloma, and preferably desmoid tumors.

The present disclosure provides crystalline polymorphs of Nirogacestat salts for use in medicine, including as an antitumor agent (in particular; in patients suffering from desmoid tumors, ovarian granulosa cell tumors, or relapsed or refractory multiple myeloma, and preferably desmoid tumors).

The present disclosure also encompasses the use of crystalline polymorphs of Nirogacestat salts of the present disclosure for the preparation of pharmaceutical compositions and/or formulations.

In another aspect, the present disclosure provides pharmaceutical compositions comprising any one or a combination of the crystalline polymorphs of Nirogacestat salts according to the present disclosure.

The present disclosure includes processes for preparing the above mentioned pharmaceutical compositions. The processes include combining any one or a combination of the crystalline polymorphs of Nirogacestat salts with at least one pharmaceutically acceptable excipient.

The crystalline polymorphs of Nirogacestat salts as defined herein and the pharmaceutical compositions or formulations of the crystalline polymorphs of Nirogacestat salts may be used as medicaments, such as for the treatment of desmoid tumors, ovarian granulosa cell tumors, or relapsed or refractory multiple myeloma, and preferably desmoid tumors.

The present disclosure also provides methods of treating desmoid tumors by administering a therapeutically effective amount of any one or a combination of the crystalline polymorphs of Nirogacestat salts of the present disclosure, or at least one of the above pharmaceutical compositions, to a subject suffering from desmoid tumors, ovarian granulosa cell tumors, or relapsed or refractory multiple myeloma, and preferably desmoid tumors, or otherwise in need of the treatment.

The present disclosure also provides uses of crystalline polymorphs of Nirogacestat salts of the present disclosure, or at least one of the above pharmaceutical compositions, for the manufacture of medicaments for treating tumors, e.g., desmoid tumors, ovarian granulosa cell tumors, or relapsed or refractory multiple myeloma, and preferably desmoid tumors.

DETAILED DESCRIPTION OF THE DISCLOSURE

Figure 1:
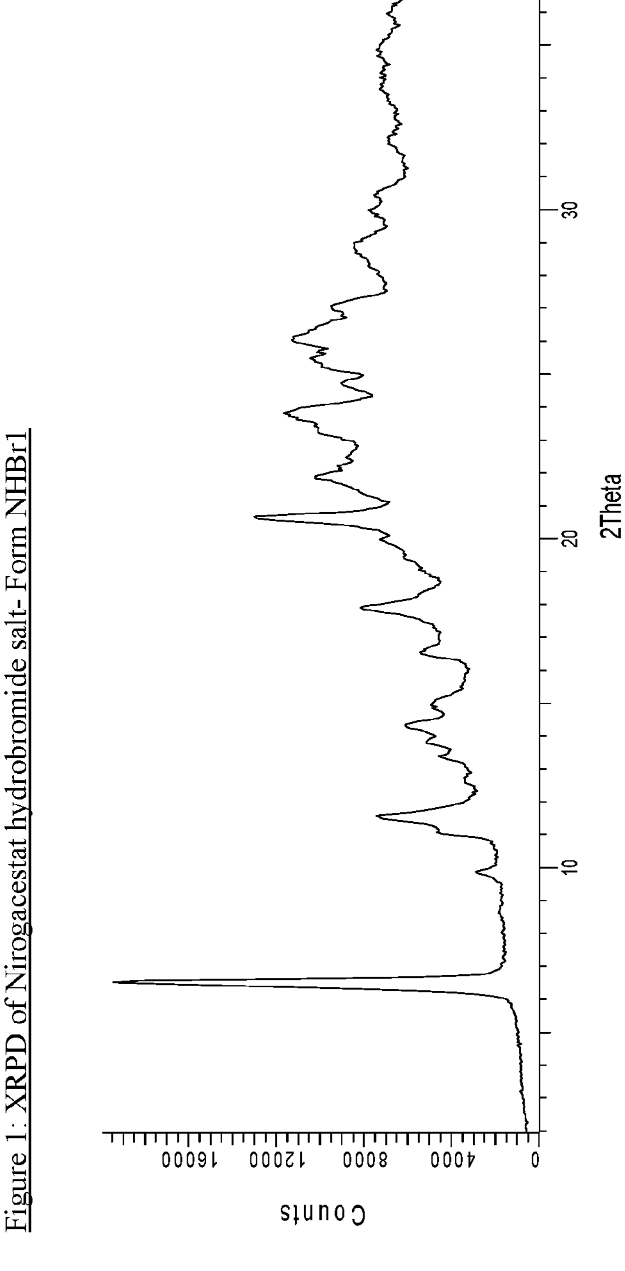
FIG. 1 shows a characteristic X-ray powder diffraction pattern (XRPD) of Nirogacestat hydrobromide salt—Form NHBr1.

The present disclosure encompasses solid state forms of Nirogacestat salts, processes for preparation thereof, and pharmaceutical compositions thereof.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Nirogacestat salts described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Nirogacestat salt. In some embodiments of the disclosure, the described crystalline polymorph of Nirogacestat salts may contain from about 1% to about 20% (w/w), from about 5% to about 20% (w/w), or from about 5% to about 10% (w/w) of one or more other crystalline polymorph of Nirogacestat and/or of Nirogacestat salt.

Depending on which other crystalline polymorphs a comparison is made, the crystalline polymorphs of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density. In particular, Form NT1 is stable for at least 6 months at high relative humidity conditions (e.g. 60% RH/25° C. and 75% RH/40° C.), and is stable for at least 7 days at exposure to relative humidities of 20%, 40%, 60% and 80%. Advantageously, Nirogacestat dihydrobromide form NT1 is stable to strong grinding, solvent drop grinding, pressure and heating up to 100° C. Therefore, Form NT1 of Nirogacestat dihydrobromide is a desirable candidate for formulations.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Nirogacestat salt referred to herein as being characterized by graphical data "as depicted in" or "as substantially depicted in" a Figure will thus be to include any crystal forms of Nirogacestat salts characterized with the graphical data having such small variations, as are well known to the skilled person, in comparison with the Figure.

As used herein, and unless stated otherwise, the term "anhydrous" in relation to crystalline forms of Nirogacestat salt which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, unless stated otherwise, the XRPD measurements are taken using copper Kα radiation wavelength 1.5418 Å. XRPD peaks reported herein are measured using CuK α radiation, λ=1.5418 Å, typically at a temperature of 25±3° C.

As used herein, unless stated otherwise $^{13}C$ NMR reported herein are measured at 700 MHz at a magic angle spinning frequency $\omega_r/2\pi$=15 kHz, preferably at a temperature of at 300 K±3° C.

A thing, e.g., a reaction mixture, may be characterized herein as being at, or allowed to come to "room temperature" or "ambient temperature," often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline polymorph of Nirogacestat hydrobromide salt-designated NHBr1. The crystalline Form NHBr1 of Nirogacestat hydrobromide salt may be characterized by data selected from one or more of the following: an X-ray powder diffraction pattern substantially as depicted in FIG. 1; an X-ray powder diffraction pattern having peaks at 6.5, 11.5, 17.9, 20.6 and 27.1 degrees 2-theta±0.2 degrees 2-theta; and combinations of these data.

Crystalline Form NHBr1 may be further characterized by an X-ray powder diffraction pattern having peaks at 6.5, 11.5, 17.9, 20.6 and 27.1 degrees 2-theta±0.2 degrees 2-theta, and also having any one, two, three or four additional peaks selected from 14.3, 15.0, 16.6 and 23.9 degrees 2-theta±0.2 degrees 2-theta.

According to any embodiment of the present disclosure crystalline form of Nirogacestat hydrobromide salt Form NHBr1 may be further characterized by: an XRPD pattern which has an absence of peaks at 0 to 6.0 degrees 2-theta±0.2 degrees 2-theta; or an XRPD pattern which has an absence of peaks at 7.0 to 7.5 degrees 2-theta±0.2 degrees 2-theta. Alternatively, according to any embodiment of the present disclosure crystalline form of Nirogacestat hydrobromide salt Form NHBr1 may be further characterized by an XRPD pattern which has an absence of peaks at 0 to 6.0 degrees 2-theta±0.2 degrees 2-theta and an absence of peaks at 7.0 to 7.5 degrees 2-theta±0.2 degrees 2-theta.

In one embodiment of the present disclosure, crystalline Form NHBr1 of Nirogacestat hydrobromide salt is isolated.

Crystalline Form NHBr1 is a monohydrobromide salt.

Crystalline Form NHBr1 may be anhydrous form.

Form NHBr1 of Nirogacestat hydrobromide is stable under all stress conditions (e.g., under strong grinding, pressure of 2 tons and at high temperature (up to 100° C.)).

Figure 2:
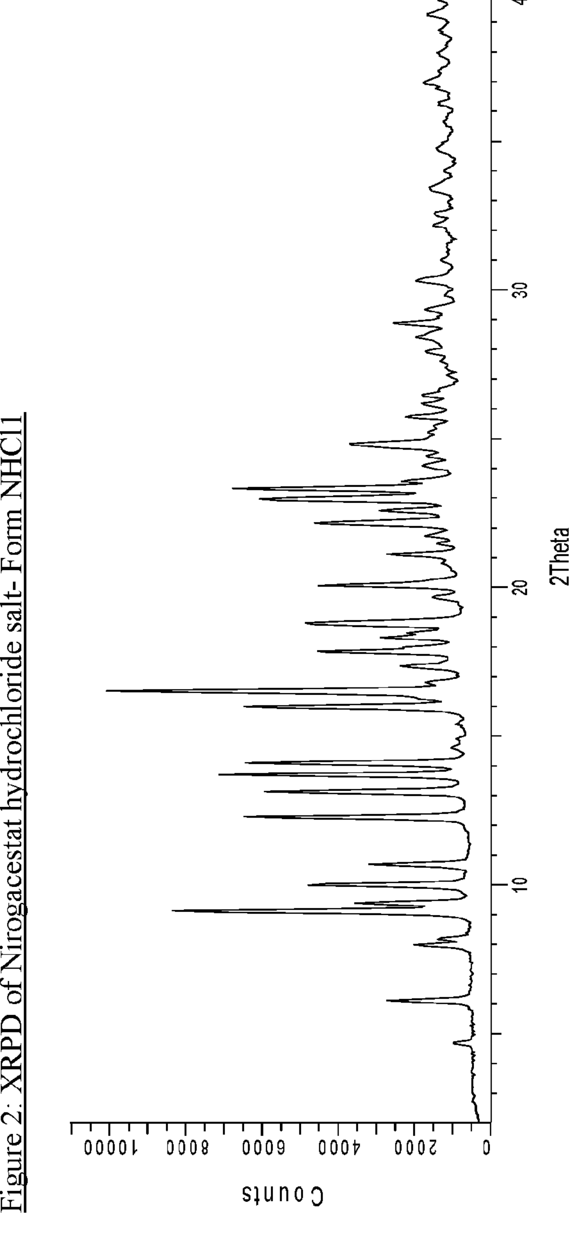
FIG. 2 shows a characteristic XRPD of Nirogacestat hydrochloride salt—Form NHCl1.

In another embodiment, the present disclosure includes a crystalline polymorph of Nirogacestat hydrochloride salt-designated NHCl1. The crystalline Form NHCl1 of Nirogacestat hydrochloride salt may be characterized by data selected from one or more of the following: an X-ray powder diffraction pattern substantially as depicted in FIG. 2; an X-ray powder diffraction pattern having peaks at 6.1, 10.7, 12.3, 14.1 and 16.0 degrees 2-theta±0.2 degrees 2-theta; and combinations of these data.

Crystalline Form NHCl1 of Nirogacestat hydrochloride salt may be further characterized by an X-ray powder diffraction pattern having peaks at 6.1, 10.7, 12.3, 14.1 and 16.0 degrees 2-theta±0.2 degrees 2-theta, and also having any one, two, three or four additional peaks selected from 9.1, 16.5, 20.1 and 24.8 degrees 2-theta±0.2 degrees 2-theta.

In one embodiment of the present disclosure, crystalline Form NHCl1 of Nirogacestat hydrochloride salt is isolated.

Crystalline Form NHCl1 may be anhydrous

In another embodiment, the present disclosure includes a crystalline polymorph of Nirogacestat sulphate salt-designated NS1.

Figure 3:
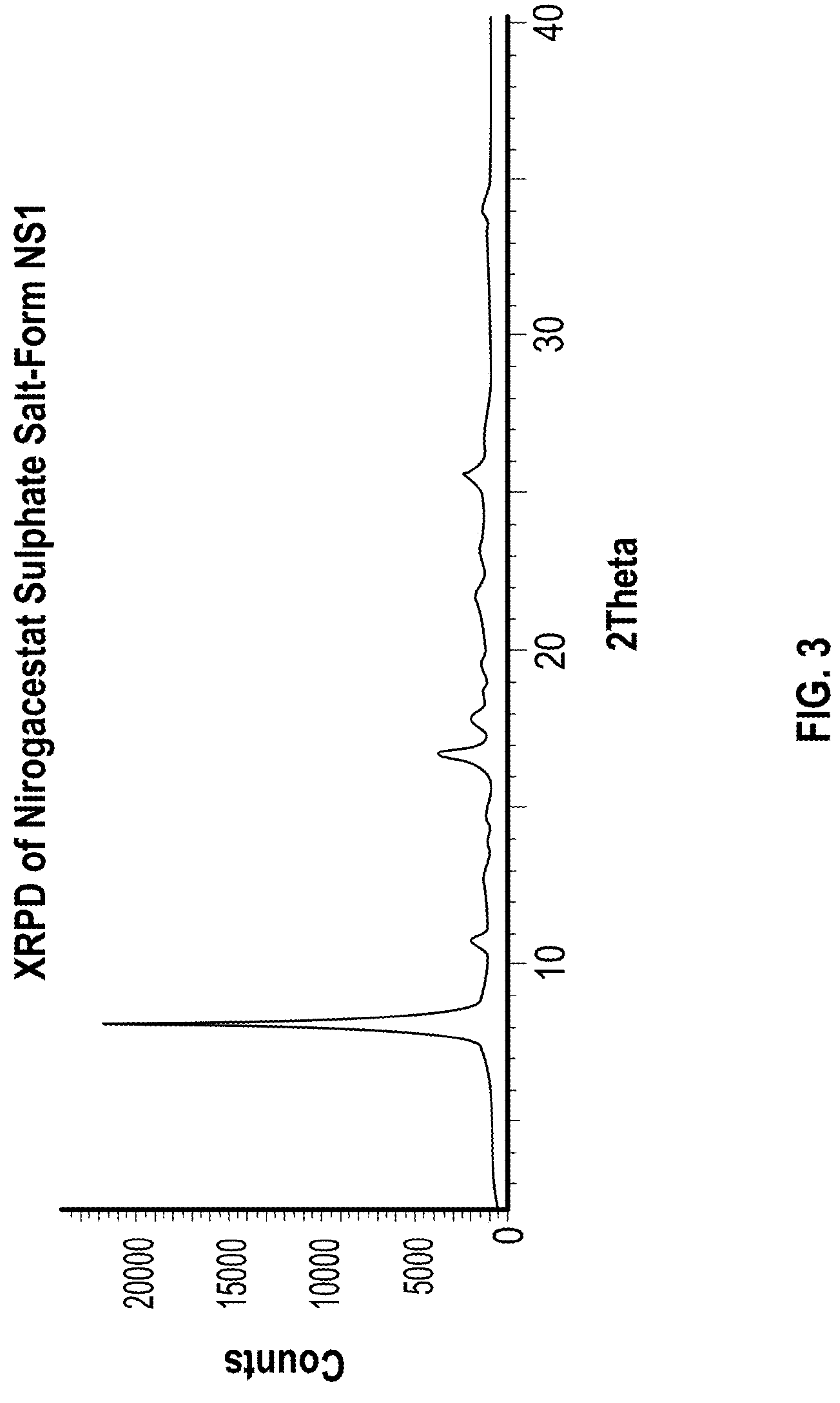
FIG. 3 shows a characteristic XRPD of Nirogacestat sulphate salt—Form NS1.

The crystalline Form NS1 of Nirogacestat sulphate salt may be characterized by data selected from one or more of the following: an X-ray powder diffraction pattern substantially as depicted in FIG. 3; an X-ray powder diffraction pattern having peaks at 8.0, 10.7, 16.6, 17.7 and 25.6 degrees 2-theta±0.2 degrees 2-theta; and combinations of these data.

Crystalline Form NS1 may be further characterized by an X-ray powder diffraction pattern having peaks at 8.0, 10.7, 16.6, 17.7 and 25.6 degrees 2-theta±0.2 degrees 2-theta, and also having any one, two, or three additional peaks selected from 21.6, 24.6 and 26.7 degrees 2-theta±0.2 degrees 2-theta.

In one embodiment of the present disclosure, crystalline Form NS1 of Nirogacestat sulphate salt is isolated.

Crystalline Form NS1 may be hydrate.

Figure 4:
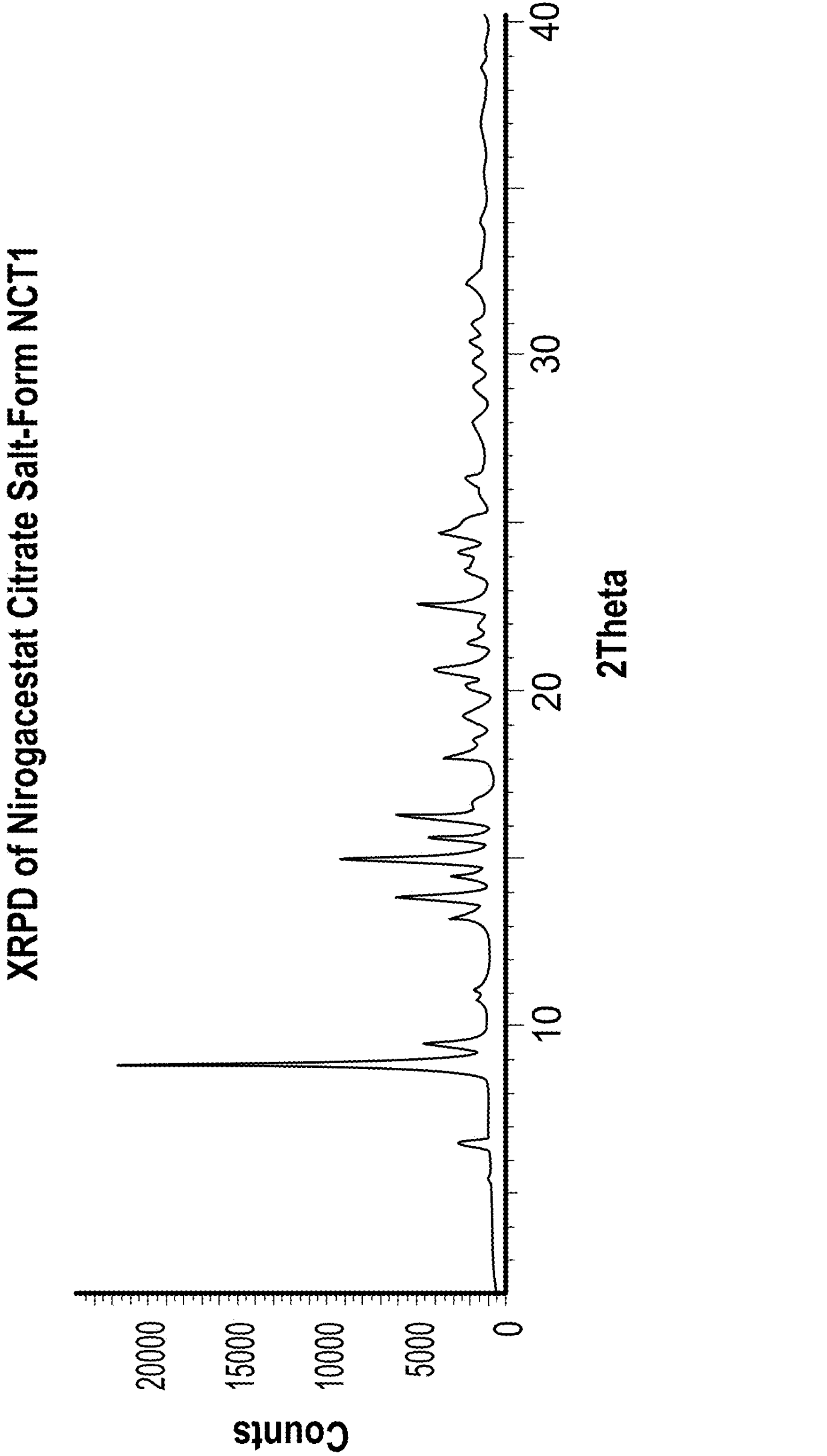
FIG. 4 shows a characteristic XRPD of Nirogacestat citrate salt—Form NCT1.

In a further embodiment, the present application discloses a crystalline polymorph of Nirogacestat citrate salt-designated NCT1. The crystalline Form NCT1 of Nirogacestat citrate salt may be characterized by data selected from one or more of the following: an X-ray powder diffraction pattern substantially as depicted in FIG. 4; an X-ray powder diffraction pattern having peaks at 8.9, 13.9, 15.0, 15.6 and 22.6 degrees 2-theta±0.2 degrees 2-theta; and combinations of these data.

Crystalline Form NCT1 of Nirogacestat citrate salt may be further characterized by an X-ray powder diffraction pattern having peaks at 8.9, 13.9, 15.0, 15.6 and 22.6 degrees 2-theta±0.2 degrees 2-theta, and also having any one, two, three, four or five additional peaks selected from 6.5, 9.5, 16.3, 20.6 and 32.1 degrees 2-theta±0.2 degrees 2-theta.

In one embodiment of the present disclosure, crystalline Form NCT1 of Nirogacestat citrate salt is isolated.

Crystalline Form NCT1 may be hydrate.

Figure 6:
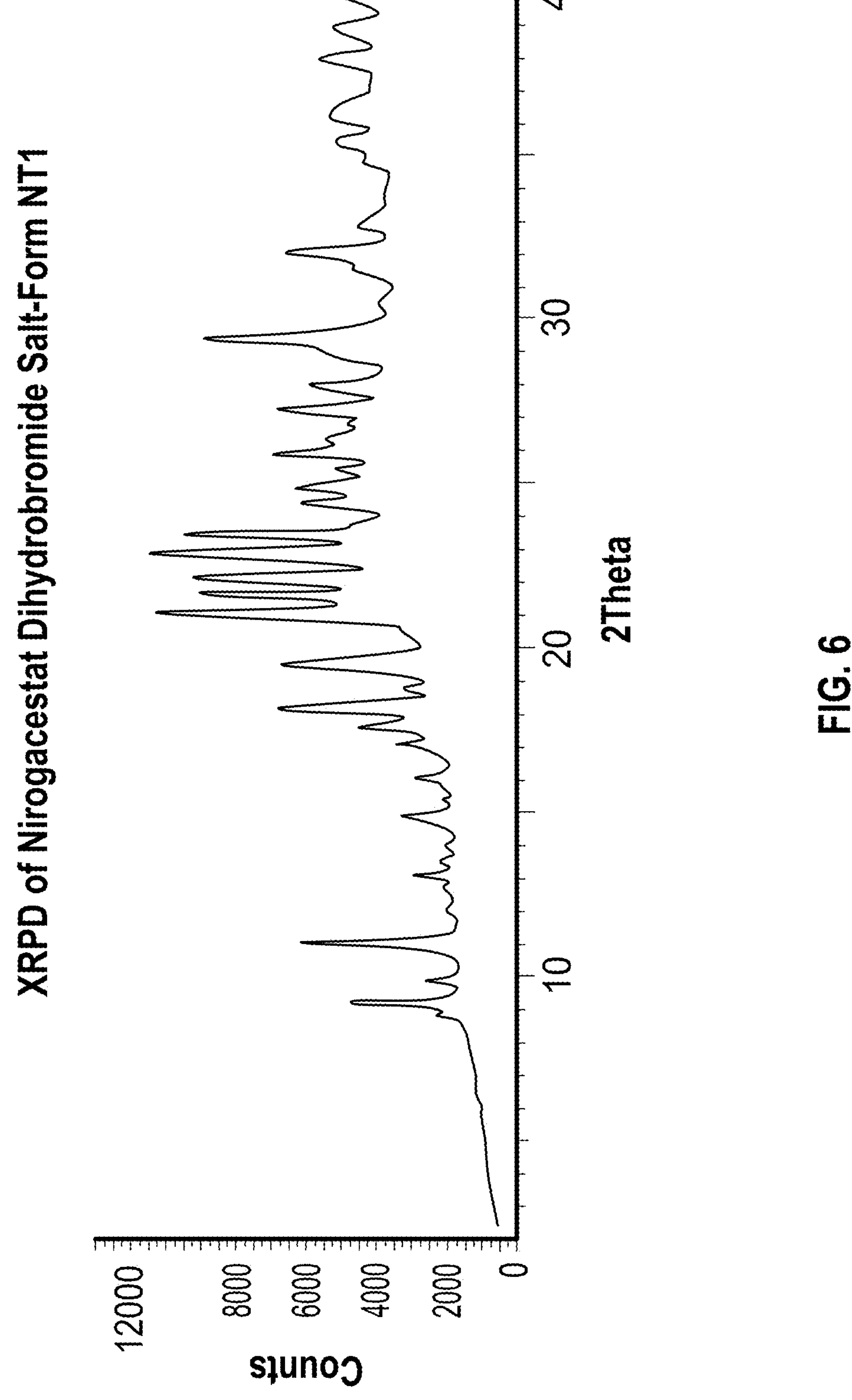
FIG. 6 shows a characteristic XRPD of Nirogacestat dihydrobromide salt—Form NT1.

Yet in a further embodiment, the present application discloses a crystalline polymorph of Nirogacestat dihydrobromide salt-designated NT1. The crystalline Form NT1 of Nirogacestat dihydrobromide salt may be characterized by data selected from one or more of the following: an X-ray powder diffraction pattern substantially as depicted in FIG. 6; an X-ray powder diffraction pattern having peaks at 10.9, 21.2, 24.5, 26.0 and 27.4 degrees 2-theta±0.2 degrees 2-theta; and combinations of these data.

Crystalline Form NT1 of Nirogacestat dihydrobromide salt may be further characterized by an X-ray powder diffraction pattern having peaks at 10.9, 21.2, 24.5, 26.0 and 27.4 degrees 2-theta±0.2 degrees 2-theta, and also having any one, two, three, four or five additional peaks selected from 9.0, 14.8, 18.8, 28.2 and 33.0 degrees 2-theta±0.2 degrees 2-theta.

Crystalline Form NT1 of Nirogacestat dihydrobromide salt may alternatively be characterized by an XRPD pattern having peaks at 9.0, 10.9, 14.8, 18.8, 21.2, 24.5, 26.0, 27.4, 28.2 and 33.0 degrees 2-theta±0.2 degrees 2-theta.

Figure 7:
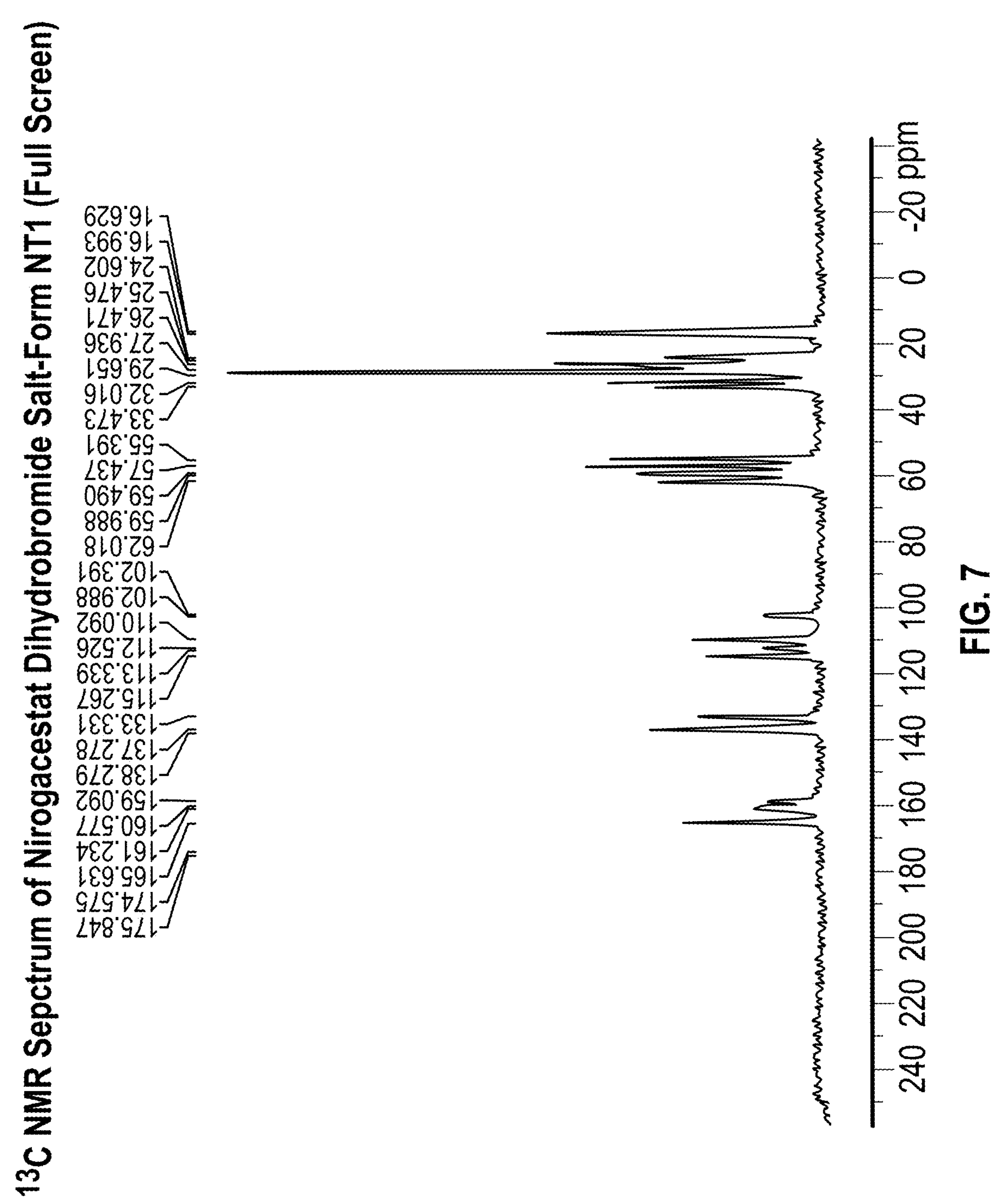
FIG. 7 shows a characteristic solid state $^{13}C$ NMR spectrum of Nirogacestat dihydrobromide salt—Form NT1 (full screen).
Figure 8:
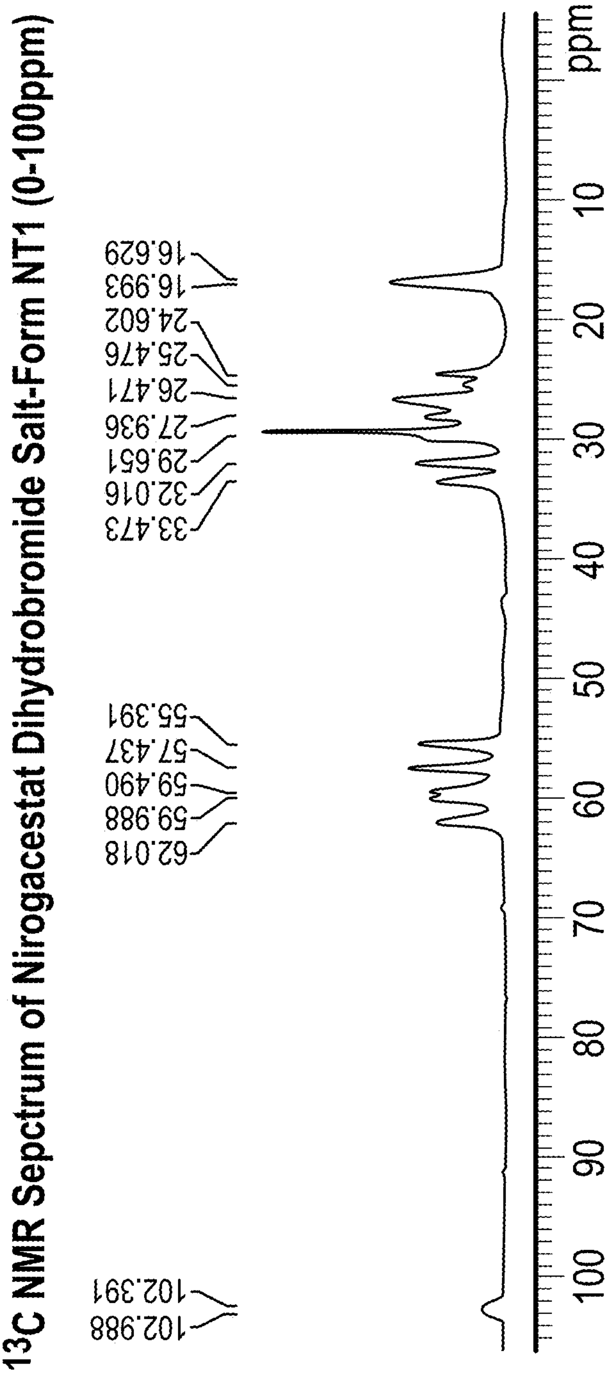
FIG. 8: Solid state $^{13}C$ NMR spectrum of Nirogacestat dihydrobromide salt—Form NT1 (0-100 ppm).
Figure 9:
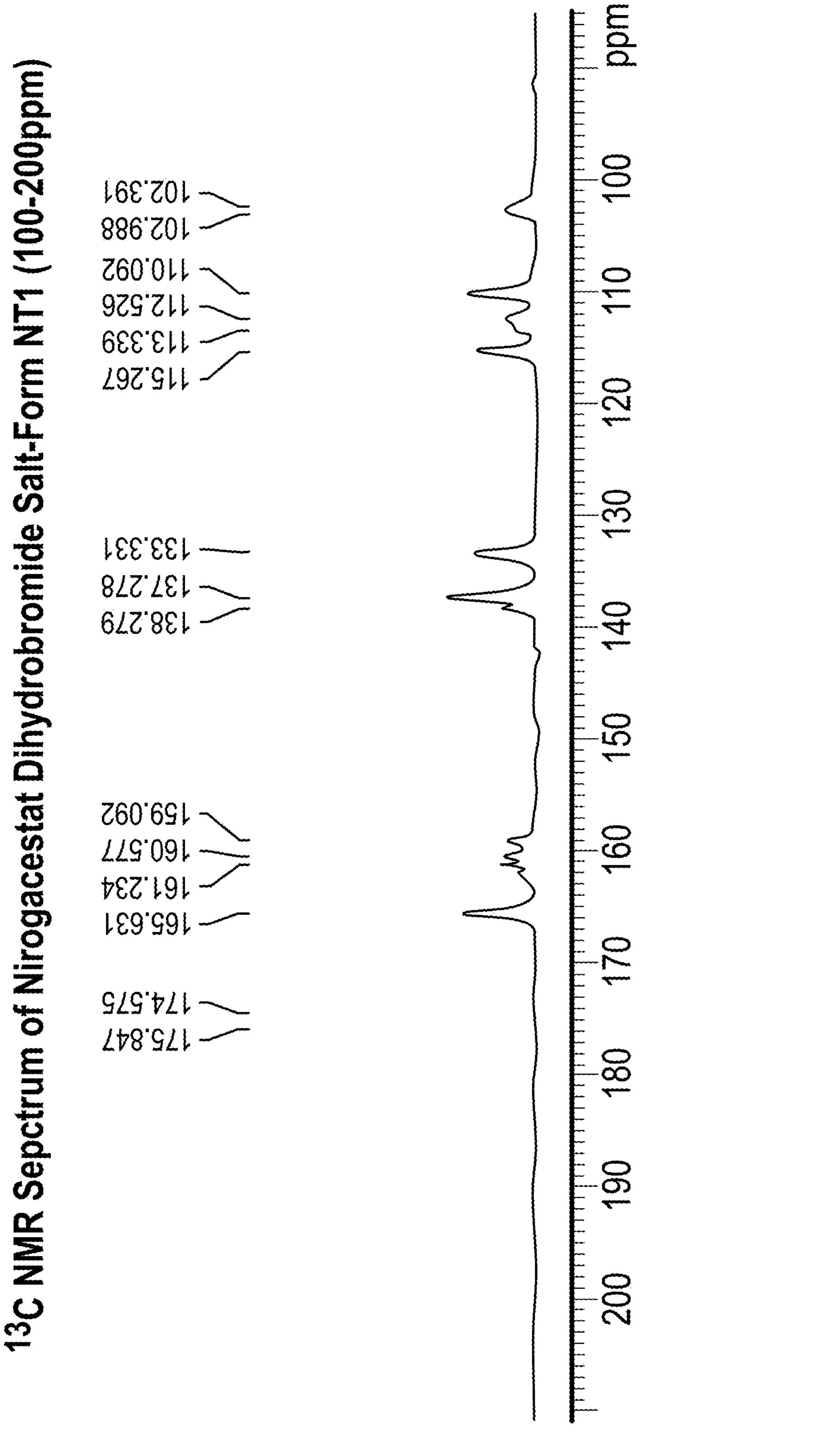
FIG. 9: Solid state $^{13}C$ NMR spectrum of Nirogacestat dihydrobromide salt—Form NT1 (100-200 ppm).

Crystalline Form NT1 of Nirogacestat dihydrobromide may be alternatively or additionally characterized by a solid state $^{13}C$ NMR spectrum with peaks at 17.0, 27.9, 55.4, 115.3, 133.3 and 165.6 ppm±0.2 ppm. Alternatively or additionally, crystalline Form NT1 of Nirogacestat dihydrobromide may be characterized by a solid state $^{13}C$ NMR spectrum having the following chemical shift absolute differences from a peak at 57.4 ppm±2 ppm of 40.4, 29.5, 2.0, 57.9, 75.9 and 108.2 ppm±0.1 ppm; optionally, Form NT1 of Nirogacestat dihydrobromide may be characterized by a solid state $^{13}C$ NMR spectrum substantially as depicted in any of FIG. 7, 8 or 9, preferably FIG. 7.

According to any embodiment of the disclosure, crystalline Nirogacestat dihydrobromide salt Form NT1 may be additionally characterized by: an XRPD pattern which has an absence of peaks at 0 to 7.5 degrees 2-theta±0.2 degrees 2-theta. Alternatively, according to any embodiment of the disclosure, crystalline Nirogacestat dihydrobromide salt Form NT1 may be additionally characterized by an XRPD pattern which has an absence of peaks at 0 to 8.0 degrees 2-theta±0.2 degrees 2-theta. Preferably, according to any embodiment of the disclosure, crystalline Nirogacestat dihydrobromide salt Form NT1 is additionally characterized by an XRPD pattern which has an absence of peaks at 0 to 8.0 degrees 2-theta±0.2 degrees 2-theta.

In one embodiment of the present disclosure, crystalline Form NT1 of Nirogacestat dihydrobromide salt is isolated.

Crystalline Form NT1 may be anhydrous.

Form NT1 of Nirogacestat dihydrobromide is stable at room temperature for at least one year and under all stress conditions (e.g., under strong grinding, pressure of 2 tons and at high temperature (up to 100° C.)).

Form NT1 of Nirogacestat dihydrobromide can be obtained from a mixture of Nirogacestat dihydrobromide in 2-butanol, wherein the mixture of Nirogacestat dihydrobromide can be obtained by reacting Nirogacestat/Nirogacestat hydrobromide with an aqueous solution of HBr in 2-butanol or by combining Nirogacestat dihydrobromide with 2-butanol.

In any aspect or embodiment of the present disclosure, any of the solid state forms of Nirogacestat salts described herein may be polymorphically pure or may be substantially free of any other solid state forms of the subject Nirogacestat salt. In any aspect or embodiment of the present disclosure, any of the solid state forms of Nirogacestat salt may contain: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or about 0%, of any other solid state forms of the subject compound, preferably as measured by XRPD. Thus, any of the disclosed crystalline forms of Nirogacestat salts described herein may be substantially free of any other solid state forms of the subject Nirogacestat salt, and may contain greater than about 80% (w/w), greater than about 90% (w/w), greater than about 95% (w/w), greater than about 98% (w/w), greater than about 99% (w/w), or about 100% of the subject solid state form of the Nirogacestat salt. As an example, Form NT1 of Nirogacestat dihydrobromide which is polymorphically pure may contain: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or about 0%, of any other solid state forms of Nirogacestat dihydrobromide, and may contain greater than about 80% (w/w), greater than about 90% (w/w), greater than about 95% (w/w), greater than about 98% (w/w), greater than about 99% (w/w), or about 100% of Form NT1 of Nirogacestat dihydrobromide.

The above crystalline polymorphs of Nirogacestat salts can be used to prepare other crystalline polymorphs of Nirogacestat, other Nirogacestat salts and solid state forms thereof.

The present disclosure provides crystalline polymorphs of Nirogacestat salts for use in the preparation of pharmaceutical compositions.

The present disclosure also encompasses the use of crystalline polymorphs of Nirogacestat salts of the present disclosure for the preparation of pharmaceutical compositions of crystalline polymorphs Nirogacestat salts and/or crystalline polymorphs thereof.

The present disclosure includes processes for preparing the above-mentioned pharmaceutical compositions. The processes include combining any one or a combination of the crystalline polymorphs of Nirogacestat salts of the present disclosure with at least one pharmaceutically acceptable excipient.

Pharmaceutical combinations or formulations of the present disclosure contain any one or a combination of the solid state forms of Nirogacestat salts of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Nirogacestat salt, and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Nirogacestat salt can be administered. Nirogacestat salt may be formulated for administration to a mammal, in embodiments to a human, by injection. Nirogacestat salt can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Nirogacestat salts, and the pharmaceutical compositions and/or formulations of Nirogacestat salts of the present disclosure, can be used as medicaments.

The present disclosure also provides methods of treating tumors by administering a therapeutically effective amount of any one or a combination of the crystalline polymorphs of Nirogacestat salts of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

X-ray diffraction was performed on X-Ray powder diffractometer: Bruker D8 Advance; CuKα radiation (λ=1.5418 Å); Lynx eye detector; laboratory temperature 22-25° C.; PMMA specimen holder ring with silicon low background. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

- Scan range: 2-40 degrees 2-theta;
- Scan mode: continuous;
- Step size: 0.05 degrees;
- Time per step: 0.5 s;
- Sample spin: 30 rpm;
- Sample holder: PMMA specimen holder ring with silicon low background.

All X-Ray Powder Diffraction peak values are calibrated with regard to standard silicon spiking in the sample.

SSNMR Method:

Solid-state NMR spectra were measured at 11.7 T using a Bruker Avance III HD 500 US/WB NMR spectrometer (Karlsruhe, Germany, 2013) with 3.2 mm probehead. The $^{13}C$ CP/MAS NMR spectra employing cross-polarization were acquired using the standard pulse scheme at spinning frequency of 11 kHz and a room temperature (300 K). The recycle delay was 8 s and the cross-polarization contact time was 2 ms. The $^{13}C$ scale was referenced to α-glycine (176.03 ppm for $^{13}C$). Frictional heating of the spinning samples was offset by active cooling, and the temperature calibration was performed with $Pb(NO_3)_2$. The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height $\Delta\upsilon_{1/2}$ was less than 3.5 Hz at 250 ms of acquisition time).

EXAMPLES

Preparation of Starting Materials

Nirogacestat can be prepared according to methods known from the literature, for example U.S. Pat. No. 7,795,447 (Example 86).

Form A of Nirogacestat diHBr can be prepared according to International Publication No. WO2021/029854.

Example 1: Preparation of Nirogacestat Hydrobromide Salt—Form NHBr1

Nirogacestat (free base, amorphous, 0.25 grams) was dissolved in acetone (4 mL) at 25° C. under stirring. Aqueous HBr solution (48%, 0.065 ml) was added dropwise into the solution at 25° C. under stirring. The reaction mass was stirred about 1 hour, filtered under vacuum and further dried for 15-30 minutes. The obtained solid was analyzed by XRPD and designated as Form NHBr1 of Nirogacestat hydrobromide salt; as shown in FIG. 1.

Example 2: Preparation of Nirogacestat Hydrochloride Salt—Form NHCl1

Nirogacestat (free base, amorphous, 0.25 grams) was dissolved in acetone (5 mL) at 25° C. under stirring. Isopropanol hydrochloride solution (18%, 0.055 mL) was added dropwise into the solution at 25° C. under stirring. The reaction mass was stirred about 55 hours, filtered under vacuum and further dried for 15-30 minutes. The obtained solid was analyzed by XRPD and designated as Form NHCl1 of Nirogacestat hydrochloride salt; as shown in FIG. 2.

Example 3: Preparation of Nirogacestat Sulphate Salt—Form NS1

Nirogacestat (free base, amorphous, 0.1 grams) was dissolved in acetone (2 mL) at 25° C. under stirring. Sulphuric acid (98%, 0.025 ml) was added into the solution at 25° C. under stirring. The reaction mass was stirred about 55 hours, filtered under vacuum, and dried for 15-30 minutes. The obtained solid was further dried in vacuum oven at 60° C. for 2 hours, and was allowed to cool down to room temperature. The obtained solid was analyzed by XRPD and designated as Form NS1 of Nirogacestat sulphate salt; as shown in FIG. 3.

Example 4: Preparation of Nirogacestat Citrate Salt—Form NCT1

Nirogacestat (free base, amorphous, 0.1 grams) was dissolved in acetone (2 mL) at 25° C. under stirring. Citric acid (40 mg) was added into the solution at 25° C. under stirring. The reaction mass was stirred about 55 hours, filtered under vacuum and dried for 15-30 minutes. The obtained solid was further dried in vacuum oven at 60° C. for 2 hours, and was allowed to cool down to room temperature. The obtained solid was analyzed by XRPD and designated as Form NCT1 of Nirogacestat citrate salt, as shown in FIG. 4.

Example 5: Preparation of Nirogacestat Dihydrobromide Salt—Amorphous

Figure 5:
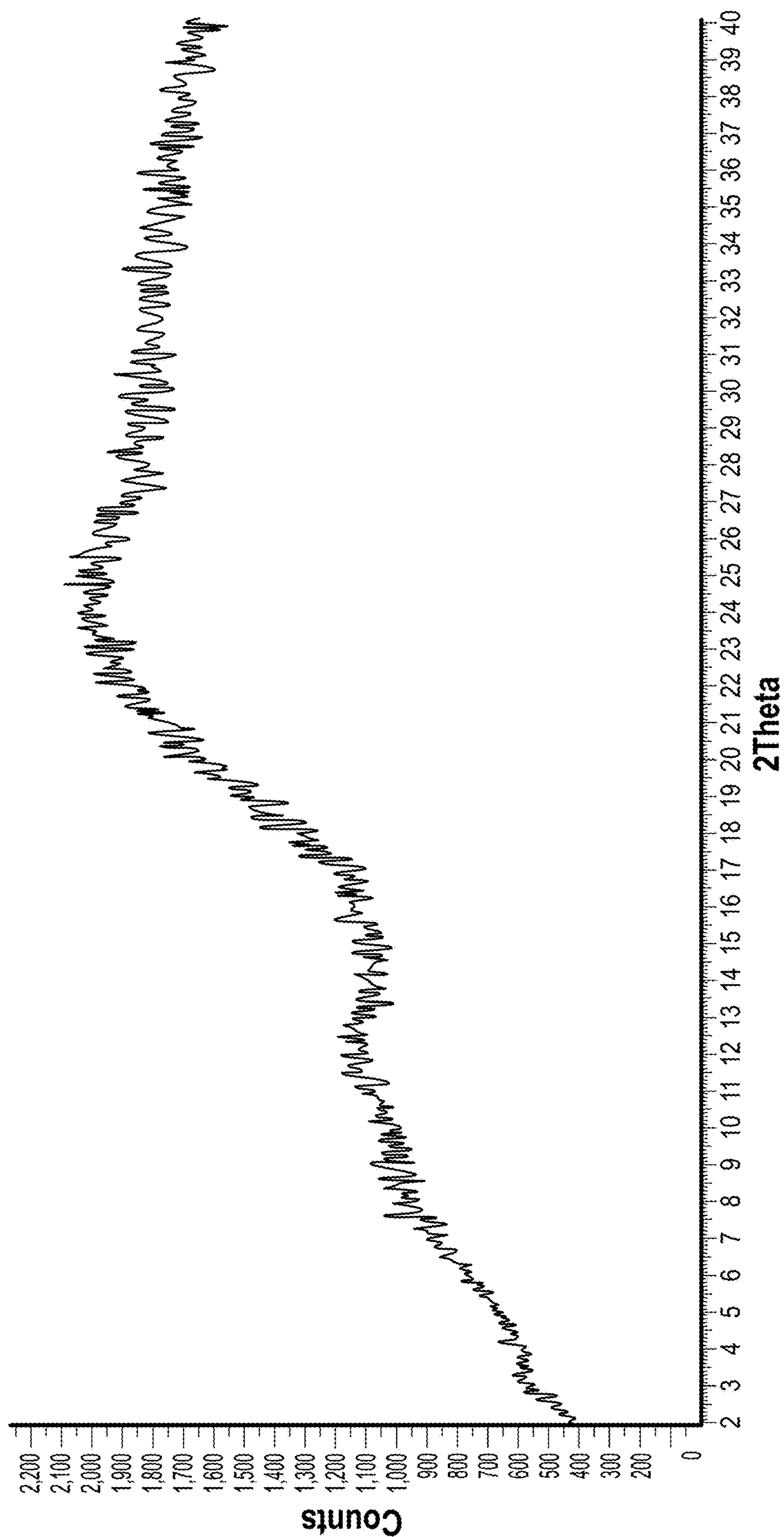
FIG. 5 shows a characteristic XRPD of amorphous Nirogacestat dihydrobromide salt.

Nirogacestat dihydrobromide (Form A, 0.5 grams) was dissolved in water (20 mL) at 60° C. The solution was filtered and the clear solution was frozen under liquid nitrogen at about 100 K. The freeze mass was subjected to lyophilization on a virtis lyophilizer (condenser temperature −76° C. and vacuum 300 mtorr) for about 18 hours. The white fluffy solid mass was isolated and analyzed by XRPD-Nirogacestat dihydrobromide-amorphous; as shown in FIG. 5.

Example 6: Preparation of Nirogacestat Dihydrobromide Salt—Form NT1

Nirogacestat hydrobromide (Form NHBr1, 0.6 grams) and 2-butanol (40 mL) were taken in a reaction tube. The reaction mixture was stirred for 5-10 minutes at 25° C., a cold (stored at 2-8° C.) aqueous HBr solution (48%, 0.22 mL) was added at 25° C. and the reaction mass was stirred overnight, and filtered under vacuum. The residue was washed with methyl tert-butyl ether (4 mL×2) and dried under vacuum at 25° C. for 15 minutes. The obtained solid was further dried in a vacuum oven at 60° C. during 18 hours and was allowed to cool down to room temperature (Yield: 0.614 G). The obtained solid was analyzed by XRPD and designated as Nirogacestat dihydrobromide salt Form NT1; as shown in FIG. 6.

Example 7: Preparation of Nirogacestat Dihydrobromide Salt—Form NT1

Nirogacestat free base (0.09 grams) was dissolved in 2-butanol (6 ml) at 25° C. The reaction mixture was stirred for 5-10 minutes and an aqueous solution HBr (48%, 11 μl) was added at 25° C. The reaction mixture was stirred for about 30 minutes. After this time, —an additional portion of aqueous solution of HBr (48%, 11 μl) at 25° C. was added and the reaction mixture was stirred about one hour and then filtered. The residue was dried under vacuum for about 15 minutes. The obtained solid was further dried in vacuum oven at 60° C. for about 18 hours. The obtained solid was analyzed by XRD and confirmed to be Form NT1 of Nirogacestat dihydrobromide salt.

Example 7: Stability Experiments

Storage Stability at Different Relative Humidities

Samples of Nirogacestat dihydrobromide Form NT1 and Nirogacestat hydrobromide Form NHBr1 were subjected to conditions of different relative humidity at ambient temperature. XRPD analysis was performed on the samples after 7 days. The results are shown in Table 1 below:

TABLE 1

| XRPD analysis | Relative humidity | | | |
|---|---|---|---|---|
| results | 20% | 40% | 60% | 80% |
| Nirogacestat dihydrobromide salt Form NT1 | No change | No change | No change | No change |
| Nirogacestat hydrobromide salt Form NHBr1 | No change | No change | No change | No change |

These results demonstrate that Nirogacestat dihydrobromide Form NT1 and Nirogacestat hydrobromide Form NHBr1 are stable after exposure to high and low relative humidity for at least 7 days.

Samples of Nirogacestat dihydrobromide Form NT1 were subjected to conditions of different relative humidity at different temperatures. XRPD analysis was performed on the samples after 6 months. The results are shown in Table 2 below:

TABLE 2

| Nirogacestat | Conditions (6 months) | |
|---|---|---|
| dihydrobromide Form NT1 | 25° C., 60% RH | 40° C., 75% RH |
| XRPD analysis results | No change | No change |

The results demonstrate that Nirogacestat dihydrobromide Form NT1 is stable after exposure to high and low relative humidity at different temperatures for at least 6 months, indicating that this crystalline form has good storage stability.

Grinding Experiments

Samples of Nirogacestat dihydrobromide Form NT1 and Nirogacestat hydrobromide Form NHBr1 were subjected to strong grinding, and to solvent drop grinding in isopropanol. Grinding was carried out on the sample alone, or in the presence of isopropanol. In these experiments, about 20 mg of the sample is placed in a mortar and ground with a pestle for 2 minutes. The solvent, when used, was added to the crystalline material before grinding, in a volume of 10 microlitres. XRPD analysis performed on the sample after the grinding experiment, confirmed no change in the starting material (Table 3):

TABLE 3

| | Nirogacestat dihydrobromide salt Form NT1 | Nirogacestat hydrobromide salt Form NHBr1 |
|---|---|---|
| Condition | XRPD analysis results | |
| Strong grinding | No change | No change |
| Solvent-drop grinding (ethanol) | No change | No change |
| Solvent-drop grinding (water) | No change | No change |

The results demonstrate that Nirogacestat dihydrobromide Form NT1 and Nirogacestat hydrobromide Form NHBr1 are resistant to polymorphic changes and are highly suitable for preparing pharmaceutical formulations.

Thermal Stability

Samples of Nirogacestat dihydrobromide Form NT1 and Nirogacestat hydrobromide Form NHBr1 were subjected to heating up to 100° C. for 30 minutes. XRPD analysis of the sample confirmed there to be no change in the starting material (Table 4):

TABLE 4

| | Nirogacestat dihydrobromide salt Form NT1 | Nirogacestat hydrobromide salt Form NHBr1 |
|---|---|---|
| Condition | Result | |
| Heating 100° C., 30 minutes | Stable | Stable |

The invention claimed is:

1. A crystalline form of Nirogacestat dihydrobromide salt designated Form NT1, which is characterized by data selected from one or more of the following:
- (a) an X-ray powder diffraction pattern substantially as depicted in FIG. 6;
- (b) an X-ray powder diffraction pattern having peaks at 10.9, 21.2, 24.5, 26.0 and 27.4 degrees 2-theta±0.2 degrees 2-theta;
- (c) a solid state $^{13}C$ NMR spectrum with peaks at 17.0, 27.9, 55.4, 115.3, 133.3 and 165.6 ppm±0.2 ppm;
- (d) a solid state $^{13}C$ NMR spectrum having the following chemical shift absolute differences from a peak at 57.4 ppm±2 ppm of 40.4, 29.5, 2.0, 57.9, 75.9 and 108.2 ppm±0.1 ppm;
- (e) a solid state $^{13}C$ NMR spectrum substantially as depicted in any of FIG. 7, 8 or 9;

and combinations of these data.

2. Crystalline Nirogacestat dihydrobromide salt according to claim 1, which is characterized by data selected from one or more of the following:
- (a) an X-ray powder diffraction pattern substantially as depicted in FIG. 6;
- (b) an X-ray powder diffraction pattern having peaks at 10.9, 21.2, 24.5, 26.0 and 27.4 degrees 2-theta±0.2 degrees 2-theta; or a combination thereof.

3. Crystalline Nirogacestat dihydrobromide salt according to claim 2, which is further characterized by a solid state $^{13}C$ NMR spectrum with peaks at 17.0, 27.9, 55.4, 115.3, 133.3 and 165.6 ppm±0.2 ppm.

4. Crystalline Nirogacestat dihydrobromide salt according to claim 2, which is further characterized by or a solid state $^{13}C$ NMR spectrum having the following chemical shift absolute differences from a peak at 57.4 ppm±2 ppm of 40.4, 29.5, 2.0, 57.9, 75.9 and 108.2 ppm±0.1 ppm.

5. Crystalline Nirogacestat dihydrobromide salt according to claim 2, which is further characterized by a solid state $^{13}C$ NMR spectrum substantially as depicted in any of FIG. 7, 8, or 9.

6. Crystalline Nirogacestat dihydrobromide salt according to claim 2, which is further characterized by an X-ray powder diffraction pattern having any one, two, three, four or five additional peaks selected from 9.0, 14.8, 18.8, 28.2 and 33.0 degrees 2-theta±0.2 degrees 2-theta.

7. Crystalline Nirogacestat dihydrobromide salt according to claim 2, which is characterized by an XRPD pattern having peaks at 9.0, 10.9, 14.8, 18.8, 21.2, 24.5, 26.0, 27.4, 28.2 and 33.0 degrees 2-theta±0.2 degrees 2-theta.

8. Crystalline Nirogacestat dihydrobromide salt according to claim 1, which is further characterized by: an XRPD pattern which has an absence of peaks at 0 to 7.5 degrees 2-theta±0.2 degrees 2-theta; or an XRPD pattern which has an absence of peaks at 0 to 8.0 degrees 2-theta±0.2 degrees 2-theta; wherein the crystalline Nirogacestat dihydrobromide salt is further characterized by an XRPD pattern which has an absence of peaks at 0 to 8.0 degrees 2-theta±0.2 degrees 2-theta.

9. Crystalline Nirogacestat dihydrobromide salt according to claim 1, which is anhydrous.

10. Crystalline Nirogacestat dihydrobromide salt according to claim 1, which is substantially free of any other solid state forms of Nirogacestat dihydrobromide salt.

11. Crystalline Nirogacestat dihydrobromide salt according to claim 1, containing about 20% (w/w) or less of any other crystalline forms of Nirogacestat and/or Nirogacestat salt.

12. Crystalline Nirogacestat dihydrobromide salt according to claim 1, containing about 20% (w/w) or less of amorphous Nirogacestat and/or Nirogacestat salt.

13. A crystalline form of Nirogacestat hydrobromide salt designated Form NHBr1, which is characterized by an X-ray powder diffraction pattern having peaks at 6.5, 11.5, 17.9, 20.6 and 27.1 degrees 2-theta±0.2 degrees 2-theta; or an X-ray powder diffraction pattern substantially as depicted in FIG. 1.

14. A crystalline form of Nirogacestat hydrobromide salt according to claim 13, which is further characterized by an X-ray powder diffraction pattern having any one, two, three or four additional peaks selected from 14.3, 15.0, 16.6, and 23.9 degrees 2-theta±0.2 degrees 2-theta.

15. A crystalline form of Nirogacestat hydrobromide salt according to claim 13, which is further characterized by: an XRPD pattern which has an absence of peaks at 0 to 6.0 degrees 2-theta±0.2 degrees 2-theta; or an XRPD pattern which has an absence of peaks at 7.0 to 7.5 degrees 2-theta±0.2 degrees 2-theta; or an XRPD pattern which has an absence of peaks at 0 to 6.0 degrees 2-theta±0.2 degrees 2-theta and an absence of peaks at 7.0-7.5 degrees 2-theta±0.2 degrees 2-theta.

16. Crystalline Nirogacestat hydrobromide salt according to claim 13, which is anhydrous.

17. Crystalline Nirogacestat hydrobromide salt according to claim 13, which is substantially free of any other solid state forms of Nirogacestat hydrobromide salt.

18. Crystalline Nirogacestat hydrobromide salt according to claim 13, containing about 20% (w/w) or less of any other crystalline forms of Nirogacestat and/or Nirogacestat salt.

19. Crystalline Nirogacestat hydrobromide salt according to claim 13, containing about 20% (w/w) or less of amorphous Nirogacestat and/or Nirogacestat salt.

20. A pharmaceutical composition comprising crystalline Nirogacestat salt according to claim 1, and at least one pharmaceutically acceptable excipient.

21. A process comprising combining crystalline the Nirogacestat salt according to claim 1 with at least one pharmaceutically acceptable excipient.

22. A medicament comprising the Crystalline Nirogacestat salt according to claim 1.

23. A method of treating tumors comprising administering a therapeutically effective amount of crystalline Nirogacestat salt according to claim 1, to a subject in need of treatment, wherein the tumors are desmoid tumors, ovarian granulosa cell tumors or relapsed or refractory multiple myeloma.

* * * * *